(12) United States Patent
Cristiani et al.

(10) Patent No.: US 9,031,657 B2
(45) Date of Patent: May 12, 2015

(54) IMPLANTABLE DEVICE FOR ACQUISITION AND MONITORING OF BRAIN BIOELECTRIC SIGNALS AND FOR INTRACRANIAL STIMULATION

(75) Inventors: Paolo Cristiani, Milan (IT); Antonino Paris, Milan (IT); Stefano Marchetti, Milan (IT); Panlaleo Romanelli, Milan (IT); Fabio Sebastiano, Milan (IT)

(73) Assignee: AB Medica S.p.A. (IT)

( * ) Notice: Subject to any disclaimer, the term of this patent is extended or adjusted under 35 U.S.C. 154(b) by 87 days.

(21) Appl. No.: 14/111,172

(22) PCT Filed: Apr. 17, 2012

(86) PCT No.: PCT/IB2012/051909
§ 371 (c)(1),
(2), (4) Date: Mar. 4, 2014

(87) PCT Pub. No.: WO2012/143850
PCT Pub. Date: Oct. 26, 2012

(65) Prior Publication Data
US 2014/0194944 A1 Jul. 10, 2014

(30) Foreign Application Priority Data
Apr. 21, 2011 (IT) .............................. RM2011A0206

(51) Int. Cl.
*A61N 1/00* (2006.01)
*A61N 1/36* (2006.01)
(Continued)

(52) U.S. Cl.
CPC .......... *A61N 1/36064* (2013.01); *A61N 1/0529* (2013.01); *A61B 5/0031* (2013.01); *A61B 5/0476* (2013.01); *A61B 5/6868* (2013.01); *A61N 1/0531* (2013.01); *A61N 1/0476* (2013.01)

(58) Field of Classification Search
CPC .............. A61N 1/0526; A61N 1/0529; A61N 1/36064; A61N 1/0531; A61N 1/0476; A61B 5/0476; A61B 5/6868; A61B 5/0031
See application file for complete search history.

(56) References Cited

U.S. PATENT DOCUMENTS 6,760,616 B2 7/2004 Hoey et al.
7,177,690 B2 * 2/2007 Woods et al. ................... 607/29
(Continued)

FOREIGN PATENT DOCUMENTS

WO WO 2005/058145 A2 6/2005
WO WO 2007/107831 9/2007
(Continued)

OTHER PUBLICATIONS

Gargiulo, G. et al., Mobile biomedical sensing with dry electrodes, Intelligent sensors, sensor networks and information processing 2008, pp. 261-266.
(Continued)

*Primary Examiner* — George Manuel
(74) *Attorney, Agent, or Firm* — Steinfl & Bruno LLP

(57) ABSTRACT

An implantable device for the acquisition and monitoring of brain bioelectric signals is described. The implantable device has a plurality of active electrodes configured to detect brain bioelectric signals, the active electrodes being arranged on a grid connected to an electronic module of the implantable device according to a predefined pattern. The active electrodes are connected to a microprocessor of the electronic module through respective paths formed on the grid and connected to at least one analog input unit arranged in the electronic module, the at least one analog input unit being in turn connected to at least one passive electrode and to the microprocessor through a data bus. The at least one analog input unit has an analog-to-digital converter for each active electrode connected thereto. A data acquisition and processing system, which includes the implantable device is also described.

12 Claims, 10 Drawing Sheets

(51) Int. Cl.
*A61N 1/05* (2006.01)
*A61B 5/00* (2006.01)
*A61B 5/0476* (2006.01)
*A61N 1/04* (2006.01)

(56) References Cited

U.S. PATENT DOCUMENTS

| | | | |
|---|---|---|---|
| 8,615,306 B2 * | 12/2013 | Griffith | ............................ 607/72 |
| 2007/0197881 A1 | 8/2007 | Wolf et al. | |
| 2008/0234598 A1 | 9/2008 | Snyder et al. | |
| 2008/0243022 A1 | 10/2008 | Donnett et al. | |
| 2009/0069866 A1 | 3/2009 | Farbarik et al. | |
| 2009/0099627 A1 | 4/2009 | Molnar et al. | |
| 2010/0160737 A1 | 6/2010 | Shachar et al. | |
| 2010/0198297 A1 | 8/2010 | Cogan et al. | |

FOREIGN PATENT DOCUMENTS

| WO | WO 2009/023488 A1 | 2/2009 |
|---|---|---|
| WO | WO 2009/029453 A2 | 3/2009 |
| WO | WO 2010/090706 A2 | 8/2010 |
| WO | WO 2010/144016 A1 | 12/2010 |

OTHER PUBLICATIONS

PCT International Search Report mailed on Jul. 11, 2012 for PCT Application PCT/IB2012/051909 filed on Apr. 17, 2012 in the name of AB Medica S.P.A.

PCT Written Opinion of the International Preliminary Examining Authority mailed on May 6, 2013 mailed on for PCT Application PCT/IB2012/051909 filed on Apr. 17, 2012 in the name of AB Medica S.P.A.

PCT Written Opinion mailed on Jul. 11, 2012 for PCT Application PCT/IB2012/051909 filed on Apr. 17, 2012 in the name of AB Medica S.P.A.

PCT International Preliminary Report on Patentability mailed on Sep. 3, 2013 for PCT Application PCT/IB2012/051909 filed on Apr. 17, 2012 in the name of AB Medica S.P.A.

* cited by examiner

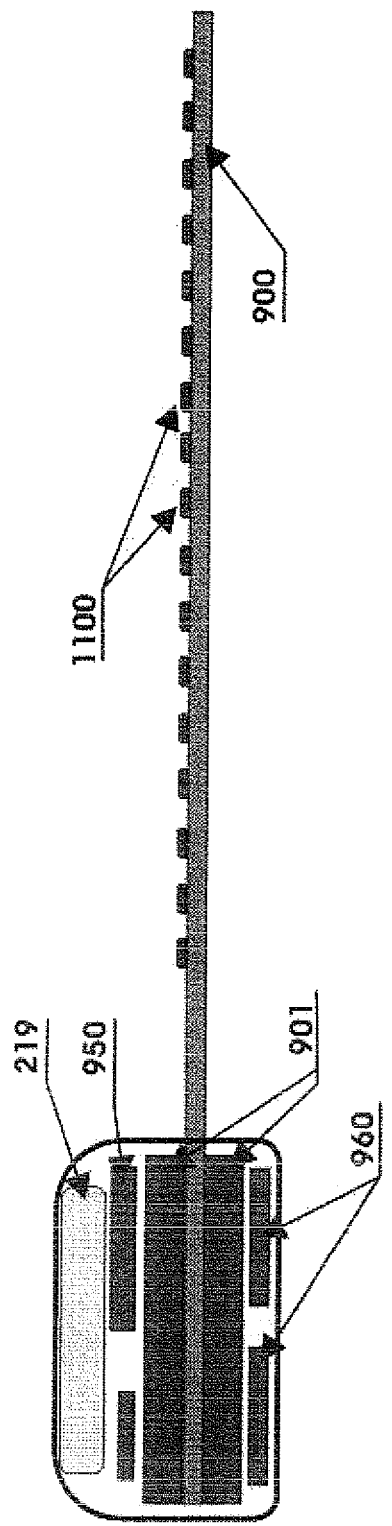

IMPLANTABLE DEVICE FOR ACQUISITION AND MONITORING OF BRAIN BIOELECTRIC SIGNALS AND FOR INTRACRANIAL STIMULATION

CROSS REFERENCE TO RELATED APPLICATIONS

The present application is the US national stage of International Patent Application PCT/IB2012/051909 filed on Apr. 17, 2012 which, in turn, claims priority to Italian Patent Application RM2011A000206 filed on Apr. 21, 2011.

The present invention relates to an implantable device for acquisition and monitoring of bioelectric signals from the brain of a patient, in particular electroencephalographic and electrocorticographic signals, as well as for intracranial stimulation. The invention also relates to a system for acquisition and processing of brain bioelectric signals comprising such an implantable device.

Within the framework of clinical neurosciences there has been a significant increase in the application of techniques for monitoring areas of the brain for diagnostic and therapeutic purposes, in particular in the treatment of drug-resistant epilepsy, Parkinson's disease, movement disorders and other psychiatric disorders such as, for example, the obsessive-compulsive disorder and chronic pain.

It is known that for the diagnosis and treatment of diseases afflicting the brain of a patient, such as epilepsy, is of fundamental importance to locate the areas, or "foci", in which these diseases originate and to make a precise mapping thereof. In the case of epilepsy, for example, those areas are called "epileptogenic zones", i.e. the set of cortical regions involved in the onset of the electrical discharge produced by neurons.

Known techniques of a non-invasive type for locating and monitoring the foci of brain diseases are, for example, electroencephalography (EEG) and magnetic resonance imaging mapping (MRI), which are based on the acquisition of bioelectrical signals through a plurality of electrodes applied on the scalp of a patient. Through these techniques it is also possible to monitor the seizures causing the typical symptoms of specific brain diseases.

Locating and monitoring techniques of an invasive type are also known, involving the use of implantable devices comprising a plurality of intracranial or intraparenchymal electrodes intended to be placed on the cortical surface or in the deep regions of the brain of a patient. These electrodes allow the acquisition of electrocorticographic signals (EcoG), providing the possibility of localizing the foci of brain diseases more accurately and of carrying out a mapping which is more detailed than the mapping that can be made by using conventional EEG signals. Thanks to the direct contact with the cortical surface or the deep regions of the brain in fact, the EcoG bioelectric signals are devoid of the typical disturbances of EEG signals, which are caused by the impedances resulting from the presence of the several layers separating the brain from the electrodes in contact with the scalp.

Locating the foci of brain diseases and defining their boundaries allow to carry out selective surgery on a patient within the limits imposed by the functional anatomy of the brain.

Recent studies in the field of epilepsy enabled to understand that the neural mechanism causing the onset of a epileptic seizure is a process of synchronizing epileptic neurons that begin to "discharge" simultaneously. Therefore, the use of implantable devices provided with electrodes has been considered not only for locating and mapping the foci of brain diseases and for monitoring the seizures, but also as a means of electrical stimulation of the brain, for example in order to prevent the neural recruitment at basis of an epileptic seizure. It is known that electrical stimulation produces an effect of desynchronization of the neurons that may prevent a seizure at the onset.

Some locating and monitoring techniques of an invasive type require the use of subcutaneous connection cables connected at one end to the electrodes of the devices implanted in the brain and at the opposite end to a data acquisition and processing system.

The presence of connecting cables coming out from the skull of a patient and connected to the processing apparatus requires hospitalization and constant monitoring of the patient, which is anyway exposed to high risks of infection. The patient is also exposed to risks of injury, for example due to the possible stripping of the connecting cables in the event of a seizure. These risks strongly limit the duration of intensive monitoring, which makes it difficult and sometimes impossible to correctly localize the foci of a brain disease.

There are also known invasive monitoring techniques based on a wireless connection between the implanted devices and the related data acquisition and processing system. The wireless connection allows to eliminate the risk of infection and injury for a patient, as subcutaneous connection cables are completely eliminated. Thanks to these features is also possible to perform monitoring of a patient for longer periods without the need for hospitalization, which allows observation of the patient under normal life conditions, when the manifestation of a seizure related to a brain disease is most likely.

An example of this kind of monitoring techniques is provided by the patent publication US 2008/0234598 A1, which discloses devices and methods for monitoring the neurological condition of patients with epilepsy. The monitoring methods are based on the analysis of physiological signals from the brain, detected by a plurality of implantable devices comprising a plurality of electrodes. The implantable devices are connected in a wireless mode to an external monitoring device, which allows storage and processing of data related to the bioelectric signals acquired. The electrodes of the implantable devices may be arranged in grid patterns comprising one or more "active" electrodes, i.e. that can acquire bioelectric signals, which are respectively connected via suitable paths to one or more "passive" electrodes, suitable to form a closed circuit with the active electrodes.

Notwithstanding the availability of acquisition and monitoring systems of bioelectric signals based on wireless implantable devices, there still exists the need to provide implantable devices and methods for locating, monitoring and mapping brain bioelectric signals, which allow to improve the locating and mapping process of the foci of a brain disease and the process of evaluating their extension, which is an object of the present invention.

It is also an object of the present invention to provide a wireless implantable device that allows to extend the monitoring period of a patient as much as possible.

Finally, it is an object of the present invention to provide an implantable device that may also be used for intracranial stimulation.

An idea of solution underlying the present invention is to provide an implantable device comprising a plurality of subdural or intraparenchymal active electrodes, i.e. electrodes suitable for detecting bioelectric signals, and at least one passive or reference electrode, wherein the electrodes are connected to an electronic module comprising a control microprocessor connected to a memory unit. The active electrodes are arranged on a grid connected to the electronic module and are individually connected to at least one analog input unit of the electronic module through suitable connections. The at least one analog input unit comprises an analog-to-digital converter for each active electrode, whereby it is possible to acquire in parallel the bioelectric signals detected by each active electrode.

In other words, the acquisition of the signals from the active electrodes is simultaneous in all the points of the grid of the implantable device, everyone of which has a precise spatial location and therefore corresponds to a uniquely defined point of the cortical surface. This allows to locate and map a focus of a brain disease very precisely, e.g. an epileptic focus, because at each instant of the acquisition period data are available of bioelectric signals detected in the whole area of the brain on which the implantable device is applied.

The grid of the active electrodes of the implantable device is preferably formed on a flexible printed circuit, while the electronic module comprises a rigid printed circuit board on which the flexible printed circuit is fixed and electrically connected. This configuration allows to house the electronic components required for the operation of the implantable device within a small size electronic module, while maximizing the contact area of the active electrodes arranged on the grid and facilitating their contact with the brain thanks to the deformability of the flexible printed circuit.

The flexible printed circuit is preferably made of polyimide and may advantageously be provided with a coating of biocompatible and non-stick material, which allows to minimize the problems of adhesion to cerebral tissues during the monitoring period of the patient, after which the device is removed. The monitoring period can thus be advantageously longer than what is currently permitted by known monitoring and acquisition devices of brain bioelectrical signals, thus paving the way for the study of brain diseases.

According to an embodiment of the invention, the active electrodes are provided with a coating having a rough surface, e.g. obtained by depositing through sublimation a layer of platinum according to the pulsed laser technology. This advantageously allows to increase the contact surface of the individual active electrodes, thereby minimizing the problems related to contact impedances and thus improving the quality of the bioelectrical signals acquired from the implantable device.

The implantable device is advantageously of a wireless type and to this aim it comprises an antenna connected to the electronic module and suitable for wireless transmission of the data related to bioelectric signals acquired by the active electrodes, which allows remote connection of the implantable device to a data acquisition and processing system comprising a base station adapted to receive data transmitted from the electronic module of the implantable device and connectable to an computer, for example a personal computer.

The data acquisition and processing system may also comprise a portable radio device adapted to receive data transmitted from the electronic module of the implantable device in order to transfer them to a computer. This configuration of the data acquisition and processing system is particularly advantageous, because it enables monitoring of the brain activity of a patient without requiring the patient to remain in the vicinity of a radio base station.

According to a further aspect of the invention, the monitoring and acquisition device may also be used for brain stimulation by way of electrical pulses, which is particularly advantageous in the preventive treatment of the seizures typical of brain diseases in combination with the long monitoring periods provided by the structural features of the device.

Brain stimulation is preferably localized, performed by identifying a focus through a warning signal and by activating only the electrodes located in this region of the brain.

To this aim, the control microprocessor of the implantable device may be programmed to generate electrical pulses and comprises a digital-to-analog converter connected to one or more of the active and/or passive electrodes through an amplifier and at least one switch.

The possibility of using the device for brain stimulation in a localized manner and to leave the device in situ for extended periods of time provides the additional advantage of allowing the development of brain-computer interfaces, for example for rehabilitation purposes following ischemic episodes or for the treatment of chronic neuropsychiatric diseases such as e.g. drug abuse, anorexia, bulimia and depression.

Moreover, the development of brain-computer interfaces may allow patients with severe lesions of the neurological system to control robotic devices such as, for example, exoskeletons, artificial limbs and the like, as well as transport devices such as wheelchairs for disabled people, and more generally automated devices such as doors, gates and elevators.

Further advantages and features of the implantable device for the acquisition and monitoring of brain bioelectric signals according to the present invention will become clear to those skilled in the art from the following detailed and non-limiting description of embodiments thereof with reference to the accompanying drawings in which.

Figure 1:
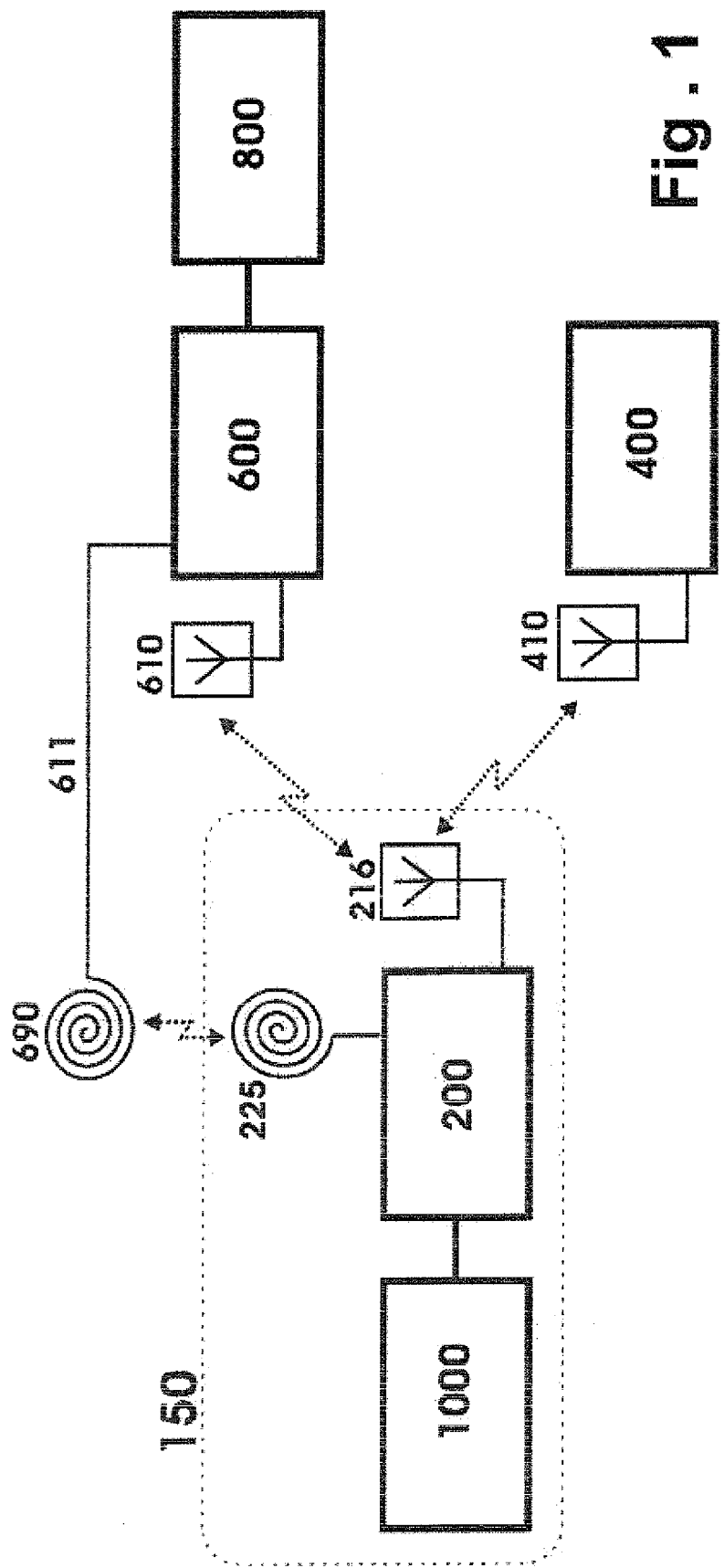
FIG. 1 shows a block diagram of a system for acquiring and processing data comprising an implantable device for the acquisition and monitoring of brain bioelectric signals according to the invention.
Figure 3A:
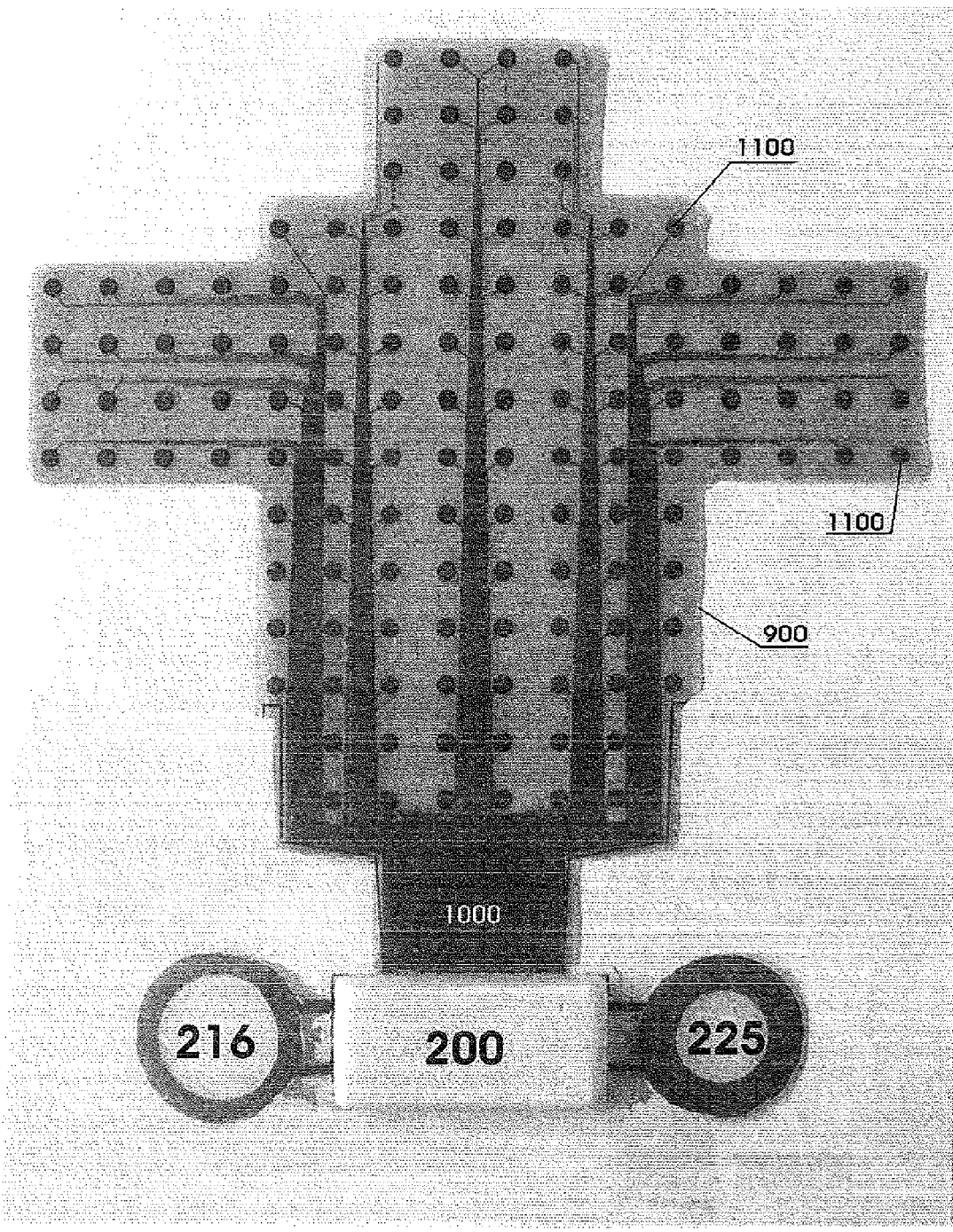
Figure 4:
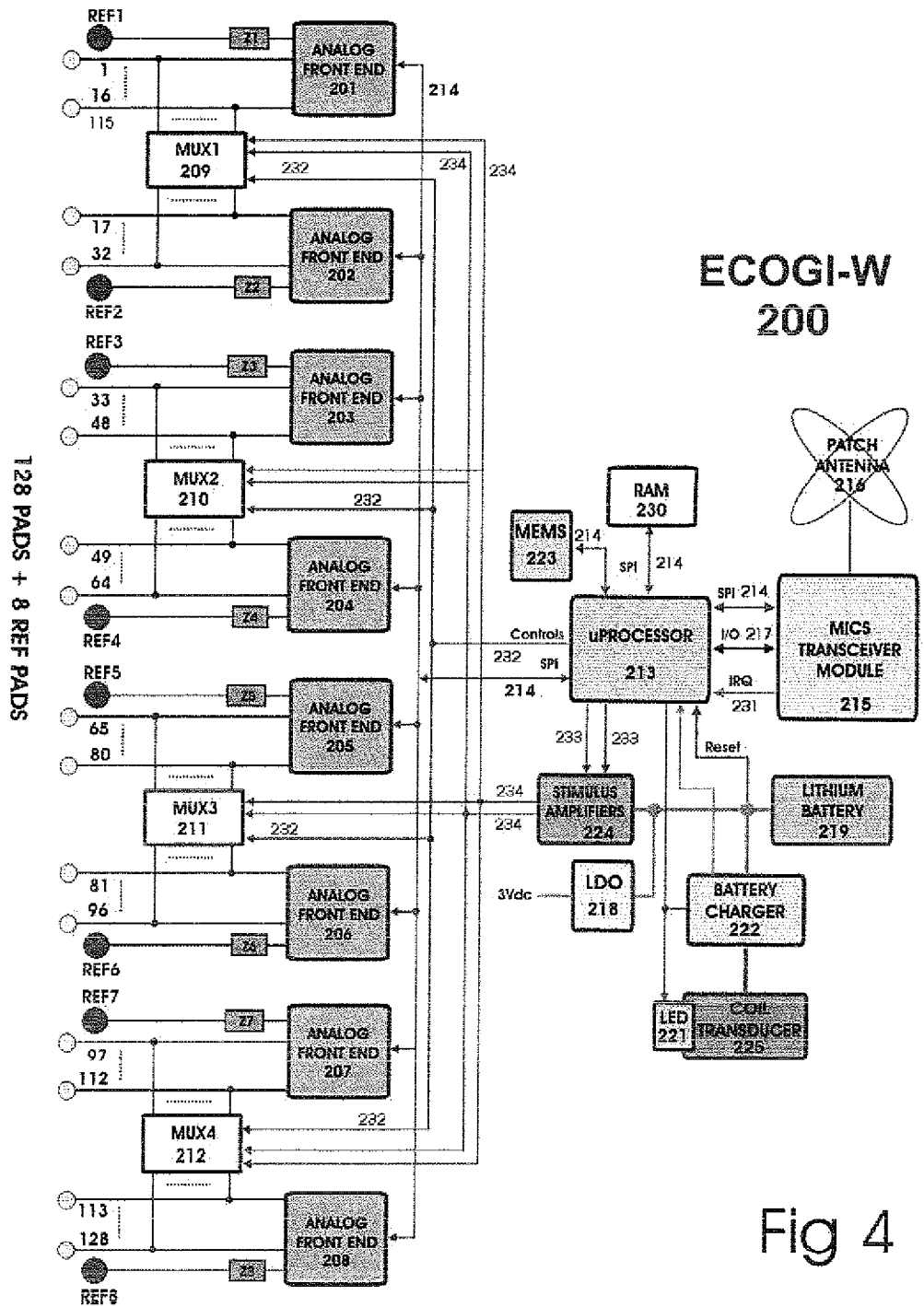
Figure 5:
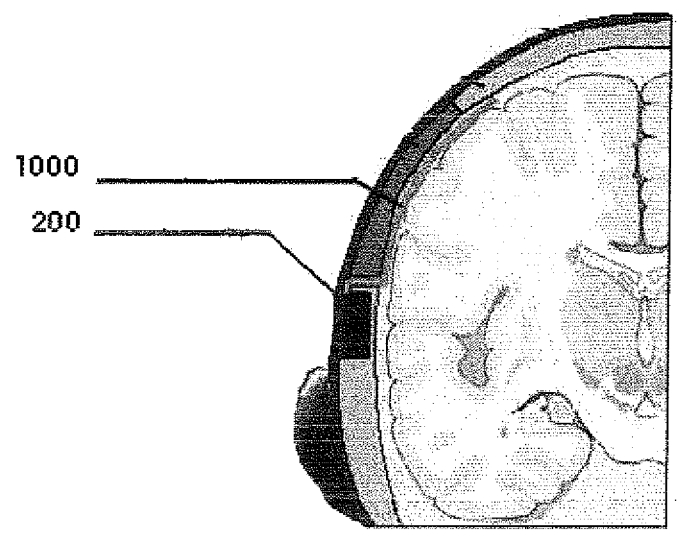
Figure 6:
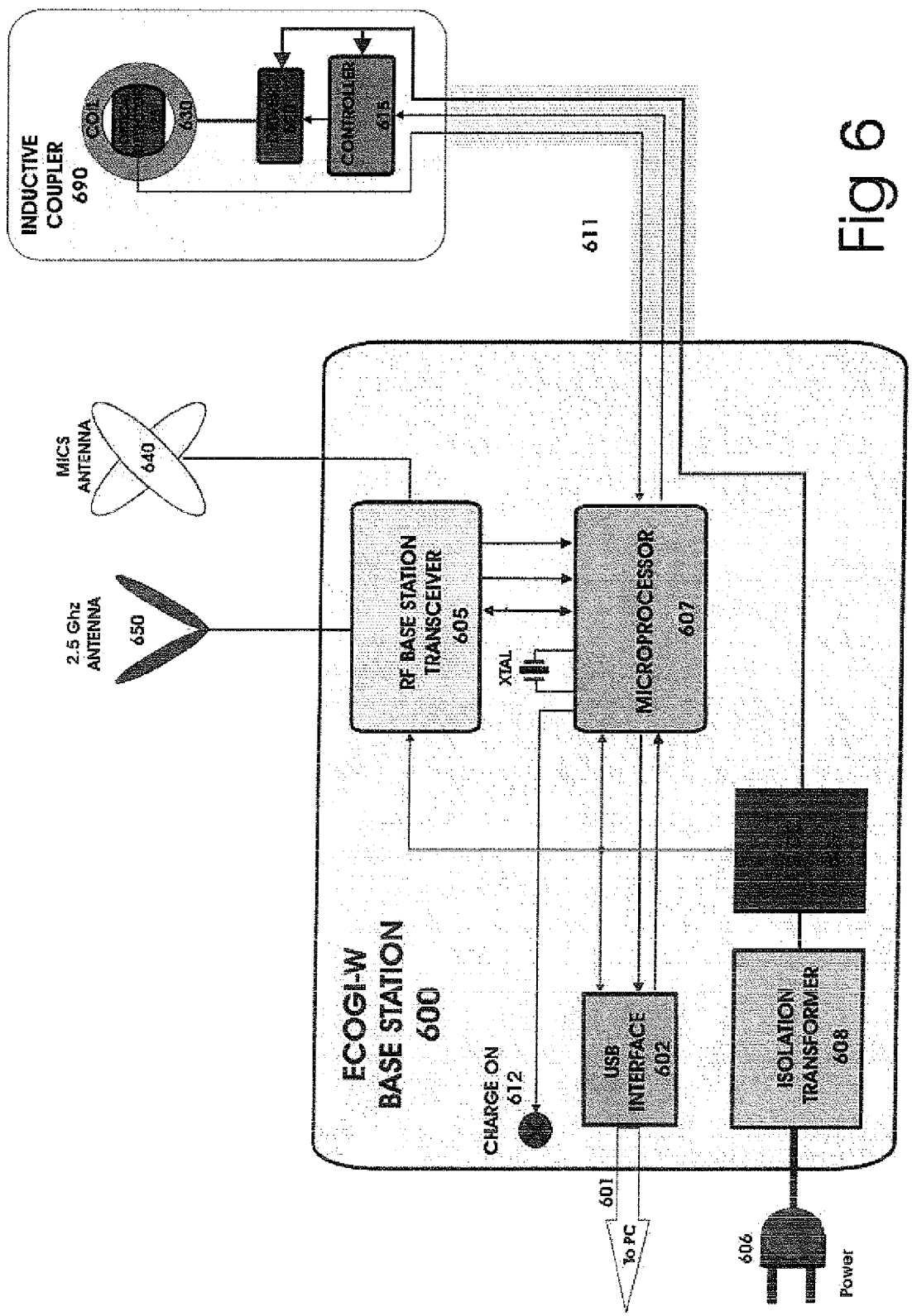
Figure 7:
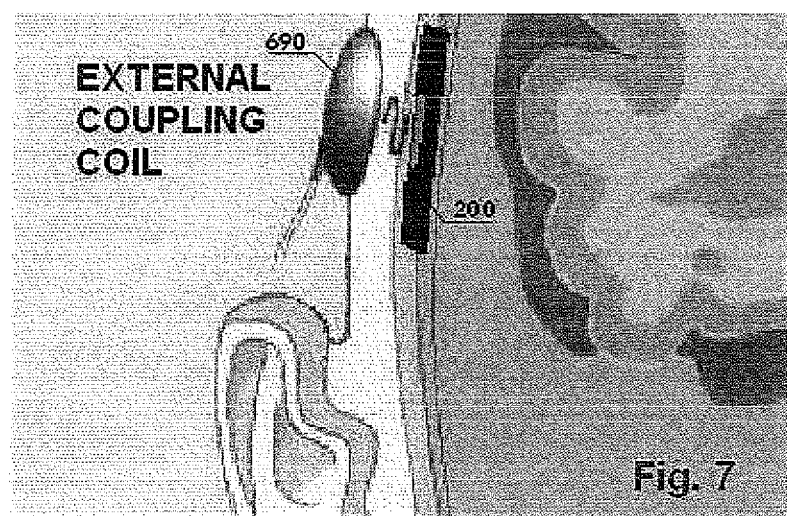
Figure 8:
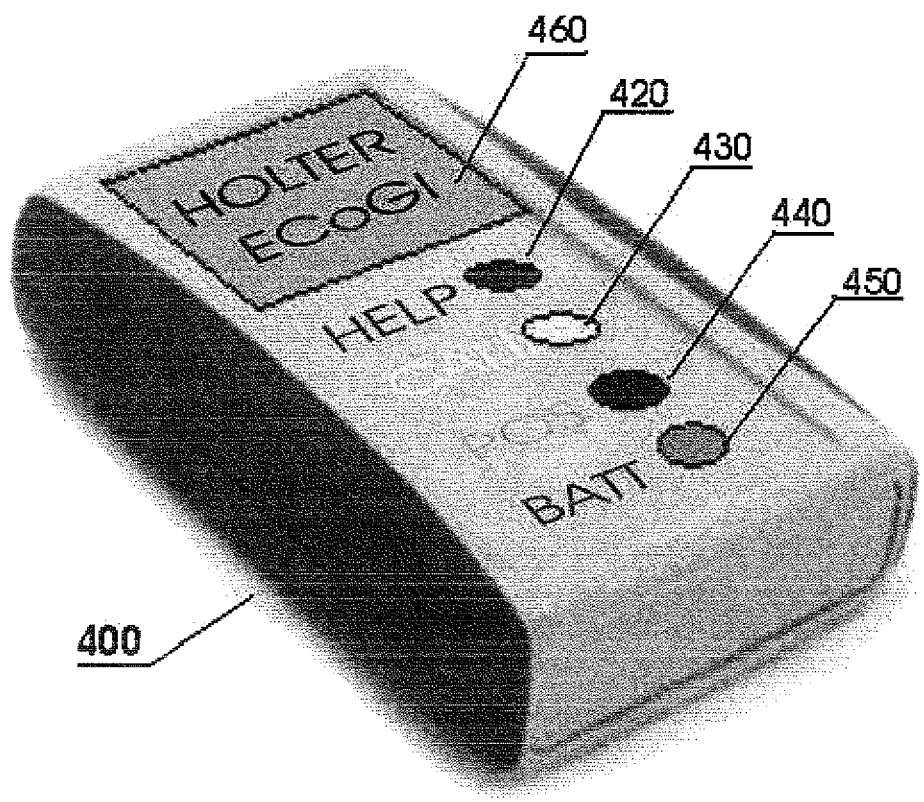
Figure 9:
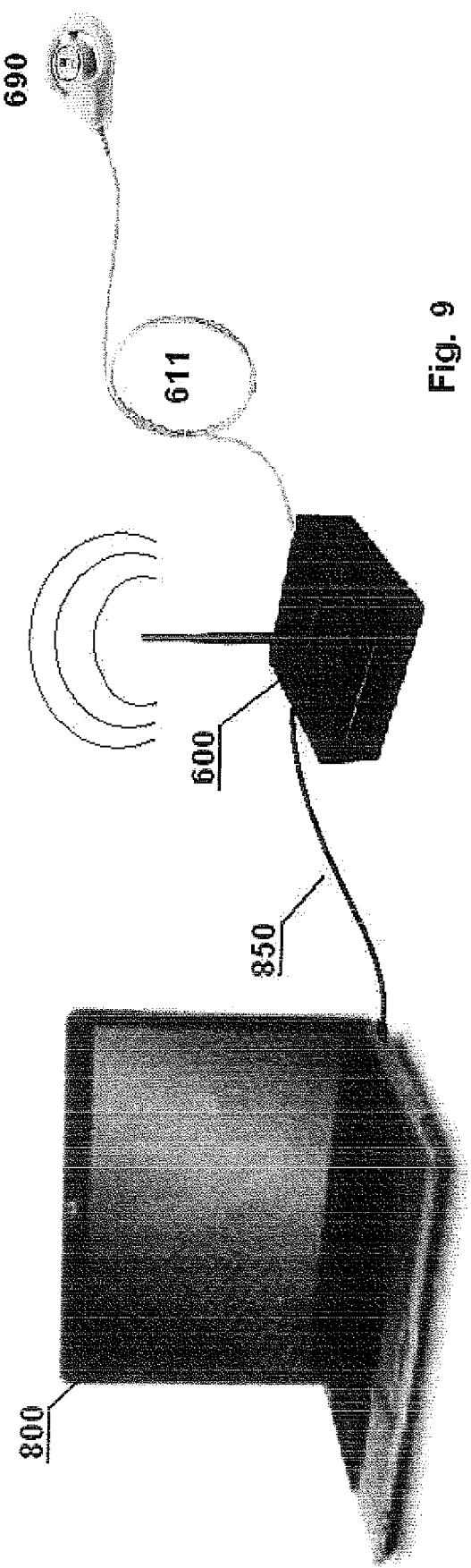

FIGS. 3a and 3b respectively show a schematic plan view from below and a schematic view in longitudinal section of the implantable device according to the invention;

FIG. 4 shows a circuit diagram of the implantable device according to the invention;

FIG. 5 shows a partial cross-sectional view of the skull of a patient in which the implantable device of the invention is implanted;

FIG. 6 shows a block diagram of a radio base station of the system of FIG. 1;

FIG. 7 shows a partial cross-sectional view similar to that of FIG. 5, wherein the implantable device is coupled to a charging device;

FIG. 8 shows a perspective view of a portable device of the system of FIG. 1, and FIG. 9 shows a schematic perspective view of a radio base station of the system of FIG. 1 connected to a computer.

Figure 2:
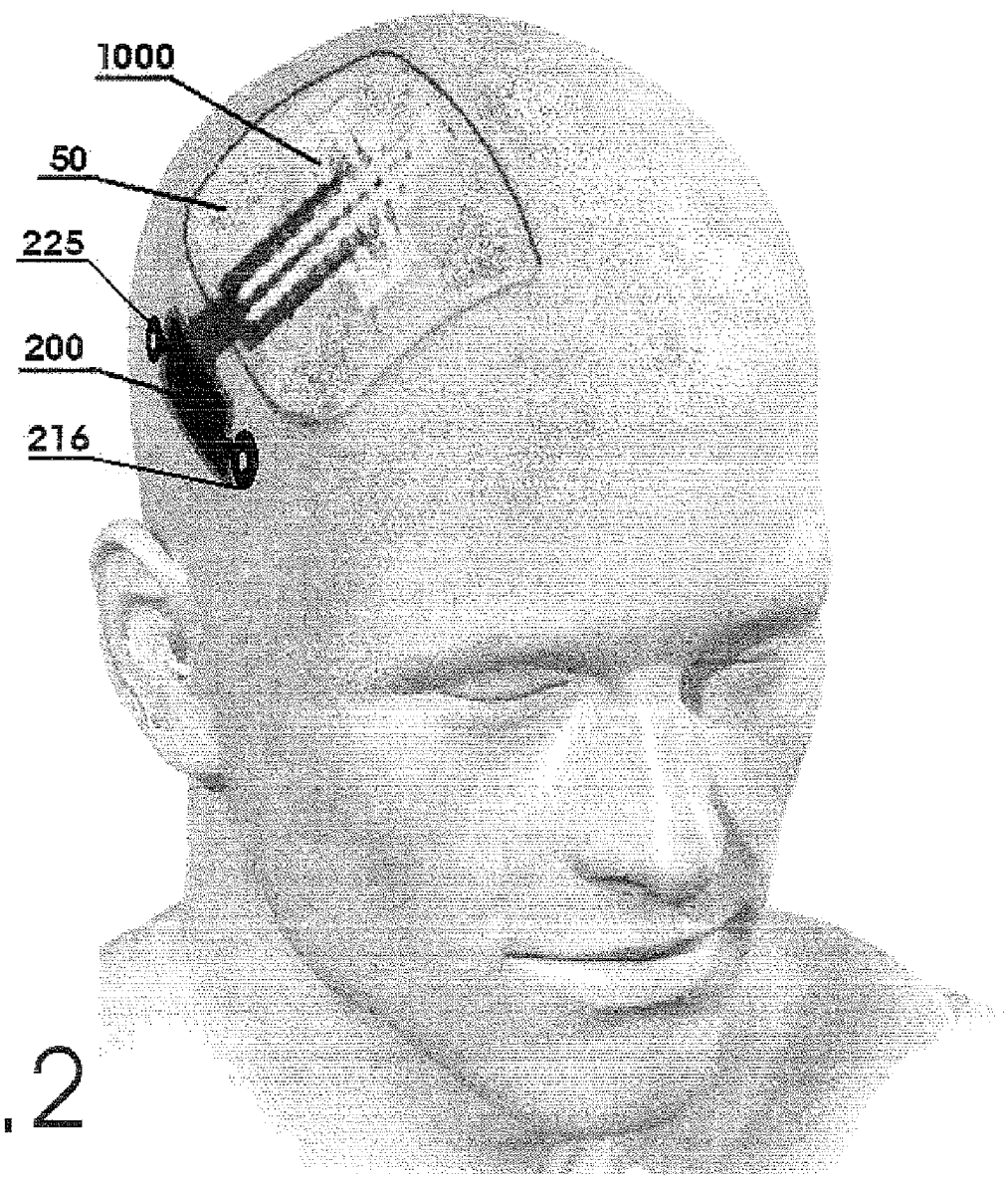
FIG. 2 shows a schematic perspective view of the implantable device of the system of FIG. 1 implanted in the skull of a patient.

FIG. 1 shows a system for acquiring and processing data comprising an implantable device, indicated with reference number 150. As shown in FIG. 2, the implantable device 150 is intended to be implanted in the skull of a patient in contact with a portion of the cortical surface.

The implantable device 150 according to the invention comprises a grid 1000 on which a plurality of active electrodes suitable for detecting brain bioelectric signals are arranged, in particular EcoG signals. The grid 1000 is connected to an electronic module 200 of the implantable device 150.

The implantable device 150 is preferably of a wireless type and to this aim it is provided with an antenna 216 connected to the electronic module 200 and suitable to allow wireless transmission of data related to bioelectric signals acquired by the active electrodes to a data acquisition and processing system. The antenna 216 is preferably of microstrip planar type.

The implantable device 150 is also provided with an energy storage system, such as a battery, preferably of a rechargeable type, housed in the electronic module 200. In order to allow charging of the battery, the implantable device 150 also comprises a winding suitable to convert picked up electromagnetic waves into an electric voltage. In the illustrated embodiment this winding is for example a magnetic transducer 225 connected to the electronic module 200.

The data acquisition and processing system suitable to receive the bioelectric signals acquired by the active electrodes of the implantable device 150 comprises a radio base station 600 connected to a computer 800, for example a personal computer, and is provided with an antenna 610 suitable to receive in a wireless mode the data relating to the brain bioelectric signals transmitted from the antenna 216 of the implantable device 150.

The radio base station 600 allows to control the operation of the implantable device 150 and to store the data acquired through the active electrodes for their further processing, and also comprises a winding configured to generate electromagnetic waves suitable to recharge the rechargeable battery of the implantable device 150 through the magnetic transducer 225. In the illustrated embodiment this winding is in particular an inductive coupler 690. The radio base station 600 can also be used for transmission of data to the implantable device 150, in particular for its electronic programming through a dedicated software.

The data acquisition and processing system may also comprise a portable device 400 provided with an antenna 410 suitable for wireless reception of the data transmitted from the antenna 216 of the implantable device 150. Similarly to the base station, the portable device 400 allows to control the operation of the implantable device 150 and to store the data relating to the acquired bioelectric signals, for example on a removable memory card suitable to allow transfer of data to a processing unit. The provision of a portable apparatus is advantageous in particular for medium/long term monitoring, as it makes the patient independent from the base station while maintaining the connection with the implantable device 150.

The radio base station 600 may be advantageously configured to communicate with the portable device 400, both to download the data stored in the memory card of the latter and to update its software.

The portable device 400, the radio base station 600 and its connections to a computer are schematically illustrated in FIGS. 8 and 9.

The wireless transmission of data related to the bioelectric signals acquired by the active electrodes is preferably carried out according to the MICS standard (Medical Implant Communications Service), in the frequency band from 402 MHz to 405 MHz. The frequencies and the radiated power define a good propagation through the tissues of the human body and cover distances, typically a few meters, which are useful to these types of application without creating risks to the health of the patient in which the implantable device 150 is implanted.

Depending on the desired monitoring period, the type of brain disease and the health condition of the patient, data transmission from the implantable device 150 may be accomplished according to a continuous or real time mode, or to a discontinuous mode, in which data are transmitted at predetermined time intervals or in response to an event typical of the patient's disease, for example an epileptic seizure.

The electronic module 200 comprises a container made of a biocompatible material within which the electronic components necessary for the operation of the implantable device 150 are housed.

Referring now to FIGS. 3a, 3b and 4, the implantable device 150 comprises a plurality of active electrodes 1100 arranged on the grid 1000 according to a predefined pattern. In the illustrated embodiment the grid 1000 has a substantially Latin cross shape at the base of which the electronic module 200 is arranged. It will be understood that the Latin cross shape of the grid 1000 is not binding in the invention and that other shapes are possible, for example designed to be adapted to particular areas of the cortical surface.

The grid 1000 is preferably made on a flexible printed circuit 900, which is elastically deformable by a force of a limited extent, allowing ease of adaptation of the implantable device 150 to the shape, in particular the curvature, of the portion of the cortical surface onto which it is applied.

As shown in FIGS. 3a and 3b, the electronic module 200 instead comprises a rigid printed circuit board 901, i.e. not elastically deformable, on which all the electronic components necessary for the operation of the implantable device 150 are mounted.

With reference to FIG. 5, while the flexible printed circuit 900 is intended to come into contact with the cortical surface, the electronic module 200 is intended to be housed in a seat formed in the skull of the patient.

FIG. 3b schematically shows an example of coupling between the rigid printed circuit board 901 and the flexible printed circuit 900. The rigid printed circuit board 901 includes in particular two portions respectively arranged on opposite faces of the flexible printed circuit 900. Reference numbers 950 and 960 schematically indicate the electronic components mounted on the rigid printed circuit board 901, while reference number 219 indicates the rechargeable battery of the implantable device 150, for example a lithium battery, suitable to supply the electronic components 950 and 960.

The magnetic transducer 225 necessary for charging the rechargeable battery 219 and the radio antenna 216 are respectively connected to the electronic module 200, for example on opposite sides thereof. These components are preferably mounted on flexible printed circuits, for example on portions of the same flexible printed circuit board 900 on which the active electrodes 1100 are arranged.

The flexible printed circuit 900 is preferably made of polyimide and is provided with a coating of biocompatible and non-stick material, which allows to minimize the adhesion problems between the implantable device 150 and brain tissues during the monitoring period of the patient, after which the implantable device 150 is generally removed. The coating of non-stick material is not applied on the active electrodes 1100, which must instead contact the brain tissue.

Among the suitable non-stick coatings, particularly effective is the use of polymers of the family of poly(para-xylylene) applied through processes of chemical vapor deposition. These polymers are already known for the coating of implantable biomedical devices, but it has been experimentally verified that they also allow to minimize the interference problems in the wireless transmission of the data related to the bioelectrical signals. Among these polymers, particularly effective is the use of the commercial product Parylene C, already known for the insulating coating of electronic circuits.

The monitoring period can thus be advantageously longer than the monitoring periods achievable with known monitoring and acquisition devices of brain bioelectrical signals, thus paving the way for the study of brain diseases and allowing to foresee the possibility of a permanent implant.

The electrodes 1100 are preferably made of a titanium-tungsten alloy and may be advantageously provided with a rough contact surface, which allows to increase the contact surface area at the interface between the active electrodes and the cortical surface, thus minimizing disturbances deriving from contact impedances. The electrodes 1100 preferably comprise a coating of a noble metal, e.g. platinum, applied by using the pulsed laser deposition technology, also known under the acronym USPLD (Ultra Short Pulsed Laser Deposition), which makes the surface porous by sublimation.

The number of active electrodes 1100 on the grid 1000 may vary depending on the size of the surface area of the cortical surface to be monitored, as well as on the desired mapping resolution, and may for example be equal to one hundred twenty eight, two hundred fifty six, one thousand twenty four and two thousand forty eight. In the illustrated embodiment one hundred twenty eight active electrodes 1100 are shown.

According to the present invention, the active electrodes 1100 are individually connected to the electronic module 200 so as to allow the acquisition of bioelectrical signals in parallel in the whole area of the portion of the cortical surface on which the active electrodes 1100 of the implantable device 150 are arranged.

The connection of the active electrodes 1100 is carried out by means of respective paths 115 formed on the grid 1000 and connected to at least one analog input unit arranged in the electronic module 200. The analog input unit is in turn connected to a microprocessor 213 of the electronic module 200 through a data bus 214, for example of serial type.

The analog input unit is also connected to at least one passive electrode and comprises an analog-to-digital converter for each active electrode 1100, which allows to acquire in parallel and simultaneously all the bioelectric signals detected by the active electrodes 1100. Each analog-to-digital converter is configured to generate digital replicas of the analog signals received from the active electrodes 1100 and the microprocessor 213 is adapted to simultaneously read the outputs of the analog-to-digital converters.

The simultaneous acquisition of bioelectrical signals from all the active electrodes 1100, everyone of which has a precise spatial location on the grid 1000 and thus corresponds to a uniquely defined point of the cortical surface, allows to obtain a remarkable accuracy in the localization of a focus of a brain disease and in its mapping, because at each detection instant data of the bioelectrical signals detected in the whole area of the cortical surface on which the implantable device 150 is applied are available.

According to an embodiment of the invention, shown in FIG. 4, the active electrodes 1100 may advantageously be divided into groups, for example eight groups of sixteen electrodes 1100, everyone of which is connected to a respective analog input unit, hereinafter referred to as AFE (Analog Front End).

In the illustrated embodiment the one hundred and twenty eight active electrodes 1100 are indicated with reference numbers 1 to 16, 17 to 32, 33 to 48, 49 to 64, 65 to 80, 81 to 96, 97 to 112 and 113 to 128, while the eight AFE are indicated with reference numbers 201 to 208. A passive electrode is associated to each group of sixteen active electrodes 1100, the passive electrodes being indicated by REF1 to REF8 and being connected to each one of the eight AFE, respectively.

As explained above, each AFE comprises an analog-to-digital converter, e.g. a 24-bit analog-to-digital converter, for each active electrode connected thereto. Each AFE further comprises for each active electrode a protective circuit on the analog input port, an amplification stage, a low-pass filter and its control logic for interfacing with the microprocessor 213 of the electronic module 200 through the data bus 214.

The data related to the bioelectric signals acquired are transmitted to the microprocessor 213, which analyzes and compresses them before transferring them to a transceiver 215 connected to the antenna 216. In order to do this, the microprocessor 213 is provided with a RAM memory 230.

With particular reference to FIGS. 4, 6 and 7, the implantable device 150 may also advantageously comprise a detection system suitable to allow locating the magnetic transducer 225 for charging the rechargeable battery 219.

In the illustrated embodiment, the locating system includes an LED 221 associated with the magnetic transducer 225 of the electronic module 200. The LED 221 is preferably arranged at the center of the magnetic transducer 225, which allows to facilitate the placement of an inductive coupler coil.

The LED 221 is preferably of an infrared type, which is known to allow a good visibility through the skin.

Being able to locate the position of the magnetic transducer 225 from the outside, it is possible to align an outer inductive coupler coil for charging the battery 219. In the illustrated embodiment, the inductive coupler 690 of the radio base station 600 comprises to this aim a coil 630.

The process of alignment between the magnetic transducer 225 and the coil 630 may advantageously be automated, thus allowing to increase the alignment accuracy for the benefit of the charging process. In the illustrated embodiment, the inductive coupler 690 is for example equipped with a photo transistor 625, operating in the same frequency band of the LED 221 and preferably arranged at the center of the coil 630. The correct alignment between the inductive coupler 690 and the magnetic transducer 225 allows to obtain the best magnetic coupling and thus the largest possible transfer of energy, that can induce on the coil of the magnetic transducer 225 a voltage higher than 5V for charging the rechargeable battery 219.

According to a further aspect of the invention, the implantable device 150 may be used not only for the acquisition of bioelectrical signals from the cortical surface, but also for its electrical stimulation, for example to prevent the epileptic seizures at their onset.

Still with reference to FIG. 4, the implantable device 150 comprises to this aim at least one digital-to-analog converter arranged inside the microprocessor 213 and programmable in order to generate electric pulses having a predefined waveform and voltage on one or more pairs of active electrodes 1100 or on one or more pairs formed of one active electrode 1100 and one passive electrode.

The electric pulses generated by the digital-to-analog converter are amplified by an amplifier 224 connected to the microprocessor 213 and arranged in the electronic module 200, and sent to at least one switch connected to a plurality of pairs of active and/or passive electrodes.

In the embodiment shown in FIG. 4, four switches are shown indicated by reference numerals 209 to 212, everyone of which comprises two sixteen paths switches that allow to send electric pulses to all the one hundred twenty eight active electrodes. The choice of the pair or pairs of active and/or passive electrodes to which the electric pulses must be sent is directly managed by the microprocessor 213 through a data bus 232, e.g. a parallel type data bus.

The embodiments of the invention herein disclosed and illustrated are only examples susceptible of numerous variants. For example, the implantable device 150 may comprise an accelerometer, e.g. an accelerometer of the MEMS type, connected to the microprocessor 213 and suitable to allow automatic detection of the movement of the patient. This further feature may be useful when the implantable device 150 is used with epileptic patients, because it allows to detect the onset conditions of an epileptic seizure, in particular convulsions, in a different way with respect to the direct acquisition of EcoG signals.

The invention claimed is:

1. An implantable device for acquisition and monitoring of brain bioelectric signals, said implantable device comprising:
    a) a plurality of active electrodes suitable to be placed in contact with a patient's brain and configured to detect brain bioelectric signals, said plurality of active electrodes being arranged on a grid connected to an electronic module of the implantable device, wherein
        the active electrodes are connected to a microprocessor of said electronic module through respective paths different from each other, are formed on said grid and are connected to analog input units arranged in the electronic module, wherein
            each analog input unit is in turn connected to a respective passive reference electrode and to said microprocessor through a data bus,
            each analog input unit is coupled to a respective set of said plurality of active electrodes and comprises an analog-to-digital converter for each active electrode of said plurality of active electrodes connected thereto, said analog-to-digital converter being configured to generate digital replicas of analog signals received from the active electrodes, said microprocessor being configured to simultaneously read outputs of the analog-to-digital converters, and
    b) at least one digital-to-analog converter arranged within the microprocessor and configured to generate electrical pulses having predetermined waveform and voltage on one or more pairs of electrodes comprising active electrodes and/or passive electrodes, the microprocessor being configured to perform brain stimulation by activating only the electrodes located in a region of the brain wherein a focus of a brain disease has been identified by simultaneously reading the outputs of the analog-to-digital converters.

2. The implantable device according to claim 1, wherein the grid is made of a flexible printed circuit and wherein the electronic module comprises a rigid printed circuit board, said flexible printed circuit being fixed and electrically connected to said rigid printed circuit board.

3. The implantable device according to claim 1, wherein a flexible printed circuit is made of polyimide and is provided with a coating of biocompatible and non-stick material, said biocompatible and non-slick material being a polymer of the family of poly(para-xylylene).

4. The implantable device according to claim 1, wherein the active electrodes are provided with a rough contact surface.

5. The implantable device according to claim 1, further comprising a transceiver and an antenna that are associated with the electronic module and suitable to allow wireless transmission of data related to the bioelectric signals acquired by the active electrodes, said antenna being connected to said transceiver which is in turn is connected to the microprocessor.

6. The implantable device according to claim 1, further comprising:
    a rechargeable battery suitable for supplying the electronic module, and
    a winding suitable for converting picked up electromagnetic waves into an electric voltage, said winding being configured to allow charging of said rechargeable battery.

7. The implantable device according to claim 6, further comprising a locating system suited to allow detection of the winding in an operative condition of the implantable device, said locating system comprising an LED associated to the winding.

8. The implantable device according to claim 7, wherein said LED is arranged at a center of the winding and is an infrared-type LED.

9. The implantable device according to claim 1, further comprising:
    an amplifier connected to the microprocessor and arranged in the electronic module, said amplifier being configured to amplify the electrical pulses generated by said at least one digital-to-analog converter, and
    at least one switch connected to the active electrodes and/or passive electrodes.

10. The implantable device according to claim 9, further comprising a data bus suitable to connect the microprocessor to the at least one switch for selection of the active electrodes and/or passive electrodes to which the electrical pulses, generated by the at least one digital-to-analog converter, are to be sent.

11. A data acquisition and processing system comprising:
    a radio base station, said radio base station being provided with an antenna suitable for wireless reception of data relating to brain bioelectric signals transmitted from an antenna of an implantable device for acquisition and monitoring of bioelectric signals, and a portable device, said portable device being provided with an antenna suitable for wireless reception and storage of data transmitted by the antenna of said implantable device, wherein the implantable device is the implantable device according to claim 1.

12. The data acquisition and processing system according to claim 11, wherein the radio base station further comprises a winding configured to generate electromagnetic waves suitable to allow recharging of the rechargeable battery of the implantable device.

* * * * *